(12) United States Patent
Yuan et al.

(10) Patent No.: US 12,428,618 B2
(45) Date of Patent: Sep. 30, 2025

(54) REACTION DEVICE FOR COMPREHENSIVE DETERMINATION OF BIODEGRADABILITY OF MATERIALS AND ITS METHOD OF USE

(71) Applicant: Nanjing University, Nanjing (CN)

(72) Inventors: Zengwei Yuan, Nanjing (CN); Yumei Wang, Nanjing (CN); Zhanlong Wang, Nanjing (CN)

(73) Assignee: Nanjing University, Nanjing (CN)

( * ) Notice: Subject to any disclaimer, the term of this patent is extended or adjusted under 35 U.S.C. 154(b) by 1178 days.

(21) Appl. No.: 17/317,243

(22) Filed: May 11, 2021

(65) Prior Publication Data

US 2022/0364040 A1 Nov. 17, 2022

(30) Foreign Application Priority Data

May 7, 2021 (CN) .......................... 202110494198.3

(51) Int. Cl.
  *C12M 1/00* (2006.01)
  *C12M 1/02* (2006.01)
  (Continued)

(52) U.S. Cl.
  CPC ............ *C12M 41/00* (2013.01); *C12M 21/16* (2013.01); *C12M 23/04* (2013.01); *C12M 23/30* (2013.01); *C12M 23/38* (2013.01); *C12M 23/48* (2013.01); *C12M 27/02* (2013.01); *C12M 29/24* (2013.01); *C12M 41/14* (2013.01); *C12M 41/18* (2013.01);
  (Continued)

(58) Field of Classification Search
  CPC ...... C12M 41/00; C12M 21/16; C12M 23/04;
  C12M 23/30; C12M 23/38; C12M 23/48;
  C12M 27/02; C12M 29/24; C12M 41/14;
  C12M 41/18; C12M 41/34; C12M 41/48;
  (Continued)

(56) References Cited

U.S. PATENT DOCUMENTS 5,890,664 A * 4/1999 Conant, III ........... C05F 17/914
                                                      241/101.76
7,762,713 B2 * 7/2010 Koh ........................ B01F 27/70
                                                      71/901
(Continued)

FOREIGN PATENT DOCUMENTS

CN                204417361 U   *   6/2015

*Primary Examiner* — Liban M Hassan
(74) *Attorney, Agent, or Firm* — PROI Intellectual Property US

(57) ABSTRACT

Provided is a reaction apparatus for comprehensively measuring biodegradability of a material, comprising a device frame, an electrical control cabinet and a reaction chamber monomer. The upper side of the reaction chamber monomer is a reaction chamber body, and the lower part is a material receiving trolley. The top of the reaction chamber body is sealed by a chamber cover. A side wall is pasted with an electric heating plate and a thermal insulation cotton. A stirring paddle is arranged inside. An air inlet and an air outlet are respectively provided on a front and a rear wall. A discharging mechanism is located below. The electrical control cabinet separately controls the reaction conditions of each reaction chamber monomer. The present invention further relates to a use method thereof, which can realize the biodegradability evaluation in such three aspects as material degradation rate, disintegration rate and ecological non-toxicity test.

5 Claims, 4 Drawing Sheets

(51) Int. Cl.
    *C12M 1/06*     (2006.01)
    *C12M 1/12*     (2006.01)
    *C12M 1/16*     (2006.01)
    *C12M 1/34*     (2006.01)
    *C12M 1/36*     (2006.01)
    *C12M 3/00*     (2006.01)
    *G01N 1/28*     (2006.01)
    *G01N 1/30*     (2006.01)

(52) U.S. Cl.
    CPC ............ *C12M 41/34* (2013.01); *C12M 41/48* (2013.01); *G01N 1/286* (2013.01); *G01N 1/30* (2013.01); *G01N 2001/2873* (2013.01)

(58) Field of Classification Search
    CPC .. G01N 1/286; G01N 1/30; G01N 2001/2873; G01N 31/22; G01N 5/04; G01N 33/00
    See application file for complete search history.

(56)     References Cited

U.S. PATENT DOCUMENTS

| | | | |
|---|---|---|---|
| 2005/0260744 A1* | 11/2005 | Campbell | C05F 17/979<br>435/290.4 |
| 2014/0044632 A1* | 2/2014 | Zielinski | B01D 53/96<br>422/111 |
| 2019/0249132 A1* | 8/2019 | Rosin | C01B 3/38 |

* cited by examiner

REACTION DEVICE FOR COMPREHENSIVE DETERMINATION OF BIODEGRADABILITY OF MATERIALS AND ITS METHOD OF USE

TECHNICAL FIELD

The present application relates to the field of measurement of biodegradability of a material, in particular to a reaction apparatus for comprehensively measuring biodegradability of a material and a use method thereof.

BACKGROUND ART

With the increasing pressure on global resources, energy conservation and environmental protection, consumers' demand for biodegradable materials is increasing. Biodegradability means that materials can be decomposed into carbon dioxide, water, mineralized inorganic salts contained in the raw materials themselves, and new biomass under the action of microorganisms. Composts are rich in microorganisms such as bacteria, fungi, actinomycetes, etc., which can reflect the biodegradability of materials in the natural environment to a certain extent, so they are listed as a recommended method for evaluating biodegradability in the world.

Domestic and foreign material degradability detection methods and related certification bodies such as ASTM, ISO, CEN, DIN Certco, etc. have proposed a plurality of indicators to comprehensively measure the biodegradability of materials, including the percentage biodegradation, the degree of disintegration and the rate of ecological toxicity. Some standards also specify related measurement methods. For example, ISO 16929: 2013 provides a method for determining the disintegration degree of plastic materials. ISO 14855 specifies a method for determining the ultimate aerobic biodegradability of plastic materials under controlled composting conditions.

However, the existing detection devices can only realize the measurement and analysis of a single index, and cannot realize the requirement of comprehensively evaluating the degradability of materials by combining multiple indexes or multiple measurement standards. In addition, the bottom of composting equipment used in the existing detection methods is generally only provided to discharge leachate, and the in and out of the materials required for the detection need to be manually loaded and unloaded from the feed inlet on the top of the equipment. Such arrangement of the existing detection equipment causes inconvenience in the operation of feeding into and discharging from the equipment. In addition, manual stirring is needed for the existing equipment in the high-temperature fermentation period of the tested materials during the detection so as to mix the reaction materials, and the odor generated during stirring will pollute the laboratory environment. Since the existing detection standards require comparison experiments with the standard degradation materials in terms of the degradation indicators so as to effectively evaluate the degradation data of the materials to be tested, a plurality of sets of apparatuses are needed to be used for simultaneous comparison experiments. A plurality of groups of independent detection apparatuses arranged side by side need to occupy a large space. If the volume of the reaction chamber containing the test material is compressed, it will be difficult to achieve high-temperature fermentation due to the limitation of volume of small piles of materials in the reaction chamber, resulting in inaccurate measurement results.

Therefore, it is necessary to design a reaction apparatus for comprehensively measuring biodegradability of a material to solve the above problems.

SUMMARY OF THE INVENTION

In view of the shortcomings of the prior art, the present application provides a reaction apparatus for comprehensively measuring biodegradability of a material and a use method therefor. The present application applies an accurate and controllable thermal insulation heating detection box system, which can meet the fermentation effects and airtightness required by material biodegradability test, so as to realize the comprehensive measurement of the biodegradability of materials. The present application specifically adopts the following technical solutions.

First, in order to achieve the above object, a reaction apparatus for comprehensively measuring biodegradability of a material is proposed, comprising: a device frame; an electrical control cabinet, which is arranged on the device frame, wherein the surface of the electrical control cabinet is provided with a control panel, and the inside of which is provided with a PLC controller; a plurality of reaction chamber monomers arranged on the device frame, wherein each of the reaction chamber monomers is connected to the electrical control cabinet, each reaction chamber monomer is independent of each other and is respectively controlled by the electrical control cabinet, wherein the reaction chamber monomer comprises: a reaction chamber body, which is arranged on the upper side inside the reaction chamber monomer, the top of the reaction chamber body is sealed by a chamber cover, materials required for measurement can be put into the reaction chamber body after the chamber cover is opened, an electric heating plate and a thermal insulation cotton are attached to the side wall of the reaction chamber body, the electric heating plate is controlled by the electrical control cabinet to adjust the temperature in the reaction chamber body; and the bottom of the reaction chamber body is provided with a discharge port for discharging the materials in the chamber; a stirring paddle, which is arranged inside the reaction chamber body, wherein the rear end of the stirring paddle is connected to a motor installed on the back side of the reaction chamber body, and the electrical control cabinet controls the operation of the motor to drive the stirring paddle to turn over the materials in the reaction chamber body; an air inlet, which is arranged on the front side wall of the reaction chamber body, wherein the air inlet is connected to the inside of the reaction chamber body for adjusting the air intake time inside the reaction chamber body according to the control signals output by the electrical control cabinet; an air outlet, which is arranged on the back side of the reaction chamber body, wherein one end of the air outlet is connected to the inside of the reaction chamber body, and the other end of the air outlet is dried by a color-changing silica gel and is then connected to a carbon dioxide detector; a discharging mechanism, comprising a leachate collection box arranged below the reaction chamber body, wherein when the leachate collection box is sealed and abuts against the discharge port at the bottom of the reaction chamber body, the leachate collection box is used for receiving the leachate produced after fermentation of the materials in the chamber; and when the leachate collection box is separated from the discharge port at the bottom of the reaction chamber body, the leachate collection box is used for discharging the fermentation material produced after fermentation of the materials in the chamber; and a material receiving trolley, which is arranged on the lower side of the inside of the reaction chamber monomer and located below the leachate collection box, wherein the top of the material receiving trolley is of an open structure for receiving the fermentation material discharged through the discharge port at the bottom of the reaction chamber body.

Optionally, the reaction apparatus for comprehensively measuring biodegradability of a material according to any of those described above, wherein the bottom of the device frame is further provided with a weight sensor at a position corresponding to each reaction chamber monomer; the outside of the reaction chamber monomer is further provided with a support frame, comprising: a side vertical plate, which is arranged on both sides of the support frame, and is connected and fixed to the side wall of the reaction chamber body; a support base plate, which is connected to the bottom of the support frame, wherein the support base plate is further provided with a sliding rail extending from back to front, the material receiving trolley moves back and forth along the sliding rail for taking out the fermentation material that falls into it or for receiving the fermentation material that falls from the reaction chamber body; and after the reaction chamber monomer is installed on the device frame, the support base plate of the reaction chamber monomer is located above the weight sensor to trigger the weight sensor to collect the weight of materials in the reaction chamber monomer and the chamber thereof.

Optionally, the reaction apparatus for comprehensively measuring biodegradability of a material according to any of those described above, wherein the chamber cover is made of a reduced resin material, and a sealing strip is provided on the lower edge of the chamber cover; a buckle is further provided between the chamber cover and the reaction chamber body, when the buckle is locked, the chamber cover and the top of the reaction chamber body are sealed and connected through the sealing strip.

Optionally, the reaction apparatus for comprehensively measuring biodegradability of a material according to any of those described above, wherein a handle is further provided on the top of the chamber cover, the side of the chamber cover is further connected with an air spring, the lower end of the air spring is connected with a cylinder hinge seat arranged on the outside of the side vertical plate, the chamber cover is driven by the air spring rotate upward to open or to rotate downward to close the reaction chamber body with a fixed supporting rotating plate arranged at the top end of the rear side of the reaction chamber body as a rotating shaft.

Optionally, the reaction apparatus for comprehensively measuring biodegradability of a material according to any of those described above, wherein the bottom of the leachate collection box is arranged to be low in the front and high in the back, the lower part of the front end of the leachate collection box is further connected with a leachate regulating ball valve, and the leachate regulating ball valve discharges the leachate received in the leachate collection box; when the leachate collection box is separated from the discharge port located at the bottom of the reaction chamber body, the stirring paddle inside the reaction chamber body rotates to drive to turn over the fermentation material in the chamber and discharge it from the discharge port into the material receiving trolley.

Optionally, the reaction apparatus for comprehensively measuring biodegradability of a material according to any of those described above, wherein one side of the leachate collection box is connected with a rotating shaft, the rear end of the rotating shaft is fixedly arranged with a gear, the gear meshes with a rack vertically arranged on the rear side of the reaction chamber body, and the upper end of the rack is fixedly connected to an electric push rod fixedly arranged on the rear side of the reaction chamber body; the electric push rod is controlled by the electrical control cabinet to extend downward or retract upward, during the downward extension of the electric push rod, the gear is driven to rotate in a first direction to drive the rotating shaft to rotate in the opening direction so that the leachate collection box rotates downwards and leaves the discharge port at the bottom of the reaction chamber body so as to make the fermentation material inside the reaction chamber body fall into the material receiving trolley; when the electric push rod is retracted upwards, the gear is driven to rotate in a second direction to drive the rotating shaft to rotate in the closing direction, so that the leachate collection box rotates upwards and closely fits the discharge port at the bottom of the reaction chamber body to close the discharge port.

At the same time, in order to achieve the above object, the present application further provides a method for using an apparatus for comprehensively measuring biodegradability of a material. The method implements the following steps by using the reaction apparatus for comprehensively measuring biodegradability of a material according to any of those described above: step 1: broking a kitchen waste into a size of 2-5 cm, adding a wood chip to a kitchen waste fragment according to a wet weight ratio of 4:1 and mixing evenly as a fermentation material, cutting a material to be tested into fragments with a size of 5 cm*5 cm, dyeing the material to be tested with a coloring agent and marking it as a test material, and mixing test material fragments with the fermentation material at a weight ratio of 1% relative to the wet weight of the fermentation material; step 2: placing a mixture of the test material and the fermentation material into a reaction chamber body of a comprehensive measurement apparatus according to any of those described above, setting a heating temperature in a corresponding reaction chamber monomer at 40° C. through a control panel, adjusting an aeration rate of an air inlet to 1.2 L/min, setting a stirring frequency of a stirring paddle to once a day, starting fermentation for composting, and receiving a leachate produced after fermentation of the test material in the chamber with a leachate collection box during fermentation; and step 3: driving a discharging mechanism to open a discharge port at the bottom of the reaction chamber body when the composting is performed to a required fertilizer age for the test, receiving the fermentation material produced the test material is fermented in the chamber with a material receiving trolley, measuring the fermentation material separately, and calculating to obtain a disintegration rate index $D_{bj}$, and a biodegradation rate index $D_{jj}$ of the test material, and an ecotoxicity index $D_{st}$ of compost product.

Optionally, a method for using a reaction apparatus for comprehensively measuring biodegradability of a material according to any of those described above, wherein the disintegration rate index $D_{bj}$ is obtained by the following steps: weighing the mass of the dyed test material in the fermentation material fragments larger than 2 mm collected by the material receiving trolley (11), comparing it with the original mass of the material to be tested added in the test, and calculating the disintegration rate index $$D_{bj} : D_{bj} = \frac{M_1 - M_2}{M_1} \times 100:$$

where, $D_{bj}$ is the disintegration rate of the test material, expressed in %; $M_1$ is the total dry solids of the test material at the beginning of the test, expressed in grams; and $M_2$ is the total dry solids in the test material collected after the test and measured after it is washed with water, expressed in grams.

Optionally, a method for using a reaction apparatus for comprehensively measuring biodegradability of a material according to any of those described above, wherein the ecotoxicity index ST is obtained by the following steps: weighing 3 g of a fresh sample of the test material after composting, adding deionized water according to wet weight/volume=1:10, placing a mixture in a constant temperature water bath shaker, adjusting the temperature to 30° C., rotating at 160 rpm, and shaking and extracting for 1 h; shaking and centrifuging an extract at 12,000 rpm at 4° C. for 25 min and passing it through a 0.45 micron filter membrane to obtain a leaching solution; adding 10 mL of the leaching solution to a petri dish, using deionized water as a control sample, and respectively sowing 10 wild celery herb seeds evenly; and culturing in a constant temperature and humidity cabinet at 20° C. for 48 hours, using the wild celery herb seeds cultured in deionized water as a control sample to determine the germination rate of the seeds and the root length of germinated seeds, and calculating the ecotoxicity index $$D_{st} = \frac{R_2 \times L_2}{R_1 \times L_1} \times 100:$$

where, $D_{st}$ is the ecotoxicity of the test material, expressed in %; $R_1$ is the germination rate of control seeds, $L_1$ is the average root length of the control seeds, $R_2$ is the germination rate of the seeds after treated in the leaching solution, and $L_2$ is the average root length of the seeds after treated in the leaching solution.

Optionally, a method for using a reaction apparatus for comprehensively measuring biodegradability of a material according to any of those described above, wherein the biodegradation rate index $D_{jj}$ is obtained by the following steps: preparing a test material and a reference material: preparing a decomposed compost with a fertilizer age of 2 to 4 months, using a thin-layer chromatography grade cellulose with a particle size of less than 20 microns as a positive control reference material, mixing it and the decomposed compost into a reference material at a standard dry weight ratio, and cutting a material to be tested into a size of 2 cm*2 cm and mixing with the same amount of the decomposed compost at the standard dry weight ratio as the test material; wherein the standard dry weight ratio of the decomposed compost in the test material and the material to be tested is 6:1; loading and fermenting for composting: placing the mixed reference material, mixed text material, and the same amount of decomposed compost without adding any material respectively into a different reaction chamber body for fermentation and composting, uniformly setting the temperature of the fermentation and composting treatment in each reaction chamber body to 58° C., and uniformly adjusting the aeration rate of the air inlet of each reaction chamber body to 1.2 L/min; measuring the biodegradation rate index $D_{jj}$: drying the air discharged from an air outlet of each reaction chamber body with a color-changing silica gel, then respectively detecting with a carbon dioxide detector the amount of carbon dioxide discharged from the mixed reference material, the mixed test material, and the same amount of decomposed compost without adding any material during the fermentation and composting, and then calculating the biodegradation rate index $D_{jj}$ according to the following formula:

$$ThCO_2 = M_{TOT} \times C_{TOT} \times \frac{44}{12}$$

$$D_{jj} = \frac{(CO_2)_T - (CO_2)_B}{ThCO_2} \times 100$$

where, $ThCO_2$ is the theoretical amount of carbon dioxide discharged from the test material, with a unit of gram per container, namely g/container; $M_{TOT}$ is the total dry solids in the test material added to the compost container at the beginning of the test, with a unit of gram; $C_{TOT}$ is the ratio of total organic carbon to the total dry solids in the test material; and 44 and 12 respectively represent the molecular weight of carbon dioxide and the atomic weight of carbon; $(CO_2)_T$ is the cumulative amount of carbon dioxide discharged from each compost container (reaction chamber monomers 1 and 2 or 3 and 4) containing the mixed test material, with a unit of grams per container, namely g/container;$(CO_2)_B$ is the average amount of carbon dioxide accumulatively discharged from the blank container (namely reaction chamber monomers 5 and 6 where the same amount of decomposed compost without adding any material is in), with a unit of grams per container, namely g/container; finally, drawing a biodegradation curve of the test material and the reference material (a relation curve of biodegradation rate and time), and reading the average biodegradation rate value from a flat part of the biodegradation curve.

Beneficial Effects (1) The present application simultaneously realizes the sealing of the reaction chamber body and the discharge of the fermentation material through the discharging mechanism. In addition, in the present application the reaction chamber body is sealed through the sealingly abutting of the leachate collection box in the discharging mechanism against the discharge opening located at the bottom of the reaction chamber body. At the same time, the stainless steel at the top of the leachate collection box is used during the closed fermentation for filtering and receiving the leachate produced after the fermentation of the material in the camber, so as to prevent the leachate from affecting the fermentation process. The present application realizes automatic discharging and automatic discharge of leachate through the design of the discharging mechanism and the material receiving trolley, which reduces manual operation;

(2) In the present application, a stirring paddle is installed inside the reaction chamber body, and the end of the stirring paddle is fixed by an plug-in flange to prevent it from being broken under pressure during the process of stirring the materials in the chamber, thereby improving the stirring efficiency. The present application also provides air tightness arrangement on the discharge port and the chamber cover of the reaction chamber body, which can directly drive the stirring paddle to mix the materials through a motor, thereby improving the convenience of operation and effectively suppressing the release of stink during stirring;

(3) In the present application, a plurality of reaction chambers are arranged on the same device frame, which can effectively use the space of the upper part (reaction in the upper part) and the lower part (discharge in the lower part)

of the reaction chamber monomer, and reduce the area occupying by the measurement apparatus. The equipment height of the present measurement apparatus is also easy to operate;

(4) The present application realizes gas supply control, temperature control and stirring control for each reaction chamber body by an electrical control cabinet, and discharges the leachate produced after fermentation of the materials in the chamber in a timely manner by a leachate collection box, which effectively protects the high-temperature fermentation of small piles of materials and improves the measurement accuracy;

(5) The present application can achieve precise control of different measurement indicators by the same set of equipment by setting different reaction temperature, air intake and stirring frequency through the electrical control cabinet. Therefore, the apparatus of the present application can be used for comprehensive evaluation of the degradability of a material to be tested.

Other features and advantages of the present application will be described in the following description, and partly become obvious from the description, or be understood by implementing the present application.

BRIEF DESCRIPTION OF THE DRAWINGS

The accompanying drawings are used to provide a further understanding of the present application, constitute a part of the description, are used to explain the present application together with the embodiments of the present application, and do not constitute a limitation to the present application. In the drawings.

Figure 1:
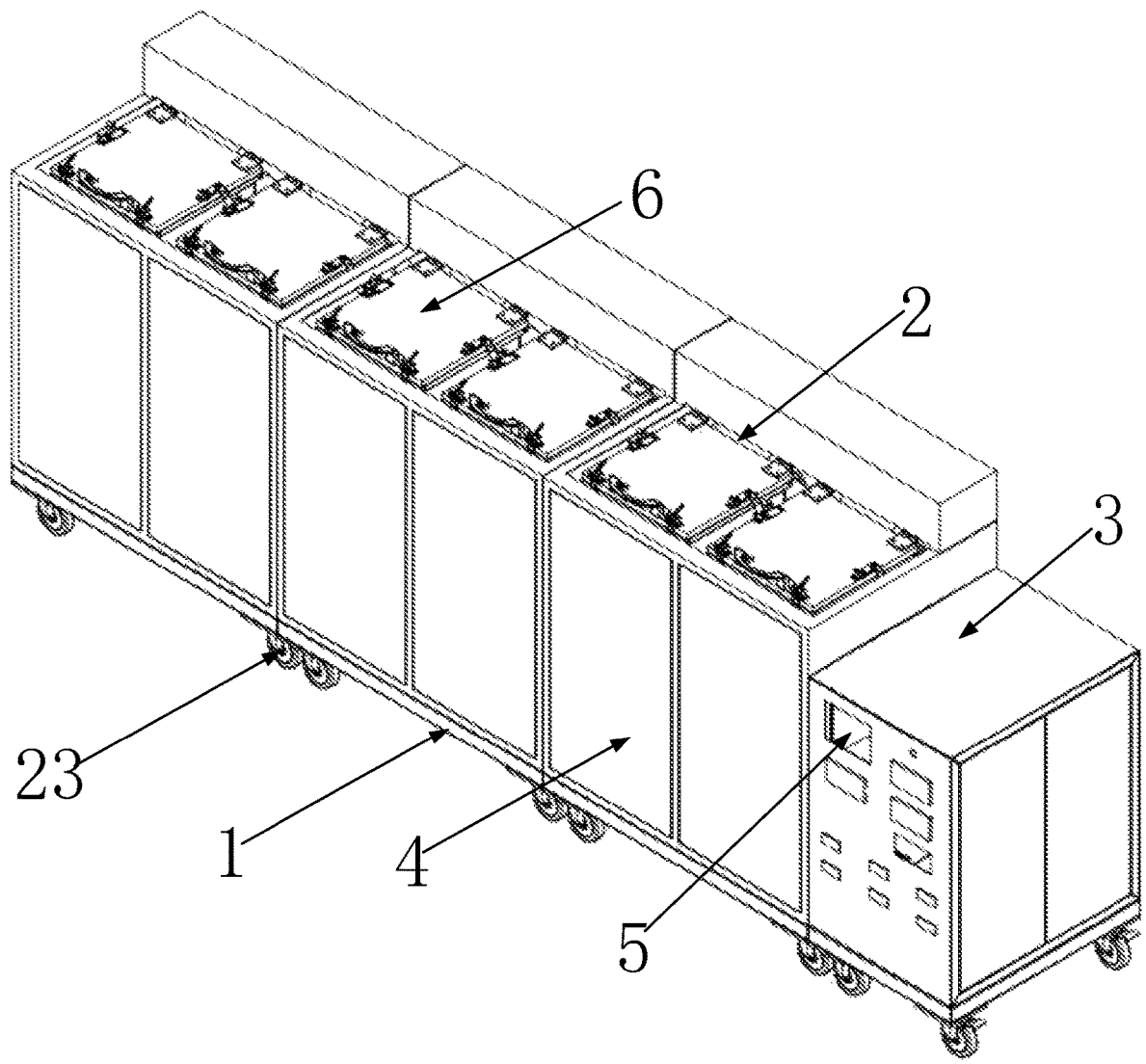
FIG. 1 is a schematic diagram of an overall structure of an reaction apparatus for comprehensively measuring biodegradability of a material according to the present application.

In the figures, 1 represents a device frame; 2 represents a reaction chamber monomer; 3 represents an electrical control cabinet; 4 represents a door panel; 5 represents a control panel; 6 represents a chamber cover; 7 represents a reaction chamber body; 8 represents a stirring paddle; 9 represents a motor; 10 represents a discharging mechanism; 11 represents a material receiving trolley; 12 represents a sliding rail; 13 represents a fixed supporting rotating plate; 14 represents a cylinder hinge seat; 15 represents an air spring; 16 represents a handle; 17 represents an electric push rod; 18 represents an air inlet; 19 represents an air outlet; 20 represents a plug-in flange; 21 represents a buckle; 22 represents a sealing strip; 23 represents an universal wheel; 24 represents a support frame; 25 represents a support bottom plate; 26 represents a side vertical plate; 27 represents a leachate collection box; 28 represents a curved stainless steel filter screen; 29 represents a leachate regulating ball valve; 30 represents a gear; and 31 represents a rack.

DETAILED DESCRIPTION

In order to make the object and technical solutions of the embodiments of the present application clearer, the technical solutions of the embodiments of the present invention will be described clearly and completely in conjunction with the accompanying drawings of the embodiments of the present application. Obviously, the described embodiments are part of the embodiments of the present application rather than all of the embodiments. Based on the described embodiments of the present utility model, all other embodiments obtained by an ordinary person skilled in the art without creative work shall fall within the protection scope of the present application.

A person skilled in the art can understand that unless otherwise defined all terms (including technical terms and scientific terms) used herein have the same meanings as commonly understood by an ordinary person skilled in the art to which the present application belongs. It should also be understood that terms as defined in general dictionaries should be understood to have meanings consistent with the meanings in the context of the prior art, and unless defined as herein, they will not be explained with idealized or overly formal meanings.

The meaning of "and/or" mentioned in the present application means that the situations where each exists alone or both exist simultaneously are included.

The meaning of "in and out" in the present application is relative to the reaction chamber monomer itself. The direction from the chamber cover to the stirring paddle inside the reaction chamber body means in, and the opposite direction means out, which is not a specific limitation to the apparatus mechanism of the present application.

The meaning of "left and right" in the present application means that when the user faces the control panel, the user's left is the left, and the user's right is the right, instead of a specific limitation to the apparatus structure of the present application.

The meaning of "connection" in the present application can be a direct connection between components or an indirect connection between components through other components.

The meaning of "up and down" in the present application means that when the user faces the control panel, the direction from the universal wheel to the chamber cover means up, and the opposite direction means down, which is not a specific limitation to the apparatus mechanism of the present application.

FIG. 1 is a reaction apparatus for comprehensively measuring biodegradability of a material according to the present application, wherein it comprises:

a device frame 1;

an electrical control cabinet 3, which is arranged on the device frame 1, wherein a control panel 5 is installed on the surface of the electrical control cabinet 3, and the inside of the control panel is provided with a PLC controller and a corresponding air supply apparatus and a motor drive circuit;

a plurality of reaction chamber monomers 2 arranged on the device frame 1, wherein each of the reaction chamber monomers 2 is respectively connected to the electrical control cabinet 3, and the reaction chamber monomers 2 are independent of each other and are respectively controlled by the electrical control cabinet 3, wherein the reaction chamber monomer 2 comprises:

a reaction chamber body 7, which is arranged on the upper side of the inside of the reaction chamber monomer 2, wherein the top of the reaction chamber body 7 is sealed by a chamber cover 6, materials required for measurement can be put into the reaction chamber body 7 after the chamber cover 6 is opened, an electric heating plate and a thermal insulation cotton are attached to a side wall of the reaction chamber body 7, the electric heating plate is controlled by the PLC controller in the electrical control cabinet 3 to supply corresponding heat according to the temperature collected by a temperature sensor arranged inside the reaction chamber body 7 so as to ensure that the temperature of a fermentation reaction in the chamber is within the range required by the measurement standard; and the bottom of the reaction chamber body 7 is provided with a discharge port for discharging the materials from the chamber;

a stirring paddle 8, which is arranged inside the reaction chamber body 7, wherein the rear end of the stirring paddle 8 is connected to a motor 9 installed on the rear side of the reaction chamber body 7, and the electrical control cabinet 3 controls the operation of the motor 9 to drive the stirring paddle 8 to turn over the materials in the reaction chamber body 7;

an air inlet 18, which is arranged on the front side wall of the reaction chamber main body 7, wherein the air inlet is connected to the inside of the reaction chamber body 7 for driving the air supply apparatus according to a control signal output by the PLC controller in the electrical control cabinet 3 so as to adjust the air intake time inside the reaction chamber body 7;

an air outlet 19, which is arranged on the rear side of the reaction chamber body 7, wherein one end of the air outlet is connected to the inside of the reaction chamber body 7, and the other end of the air outlet is dried by a color-changing silica gel and is then connected to a carbon dioxide detector for detecting the amount of carbon dioxide emitted during the fermentation reaction of the materials in the chamber;

a discharging mechanism 10, comprising a leachate collection box 27 arranged below the reaction chamber body 7, wherein when the leachate collection box 27 is sealed and abuts against the discharge port at the bottom of the reaction chamber body 7, the leachate collection box 27 is used for receiving the leachate produced after fermentation of the materials in the chamber; and when the leachate collection box 27 is separated from the discharge port at the bottom of the reaction chamber body 7, the leachate collection box 27 is used for discharging the fermentation material produced after the fermentation of the materials in the chamber;

a material receiving trolley 11, which is arranged on the lower side of the inside of the reaction chamber monomer 2 and located below the leachate collection box 27, wherein the top of the material receiving trolley 11 is of an open structure for receiving the fermentation material discharged through the discharge port at the bottom of the reaction chamber body 7.

Therefore, the present application can use kitchen waste as a substrate, control the reaction chamber monomer 2 through the electrical control cabinet to provide reaction conditions that meet the requirements of the measurement standard, and achieve comprehensive determination of the biodegradability of materials through the comparison of disintegration rate, ecotoxicity and biodegradability of the material to be tested and the reference material. For specific implementation, please refer to the following steps:

step 1: broking a kitchen waste into a size of 2-5 cm, adding a wood chip to a kitchen waste fragment according to a wet weight ratio of 4:1 and mixing evenly as a fermentation material, cutting a material to be tested into fragments with a size of 5 cm*5 cm, dyeing the material to be tested with a coloring agent and marking it as a test material, and mixing test material fragments with the fermentation material at a weight ratio of 1% relative to the wet weight of the fermentation material;

step 2: placing a mixture of the test material and the fermentation material into a reaction chamber body 7 of an aforementioned comprehensive measurement apparatus, setting a heating temperature in a reaction chamber monomer 2 of the reaction chamber body 7 at 40° C. through a control panel 5, adjusting an aeration rate of an air inlet 18 to 1.2 L/min, setting a stirring frequency of a stirring paddle 8 to once a day, starting fermentation for composting, and receiving a leachate produced after fermentation of the test material in the chamber with a leachate collection box 27 during fermentation;

step 3: when the compost is processed to the required fertilizer age for the test, driving the discharging mechanism 10 to rotate downward to open the discharge port located at the bottom of the reaction chamber body 7, at the same time driving the stirring paddle to rotate to discharge the fermentation material in the chamber through the discharge port to the material receiving trolley 11, measuring the fermentation material after the material receiving trolley 11 receives the fermentation material produced after the fermentation of the test material in the chamber, calculate to obtain the disintegration rate index $D_{bj}$ and a biodegradation rate index $D_{jj}$ of the test material, and an ecotoxicity index $D_{st}$ of compost product, and then judging the biodegradability of the test material according to the three indexes.

Wherein, the disintegration rate index BJ is obtained by the following steps:

weighing the mass of the dyed test material in the fermentation material fragments larger than 2 mm collected by the material receiving trolley 11, comparing it with the original mass of the material to be tested added in the test, and calculating the disintegration rate index $D_{bj}$:

$$D_{bj} = \frac{M_1 - M_2}{M_1} \times 100$$

where, $D_{bj}$ is the disintegration rate of the test material, expressed in %; $M_1$ is the total dry solids of the test material at the beginning of the test, expressed in grams; and $M_2$ is the total dry solids in the test material collected after the test (measured after washing with water), expressed in grams.

The ecotoxicity index $D_{st}$ is obtained by the following steps:

step S1: weighing 3 g of a fresh sample of the test material after composting, adding deionized water according to wet weight/volume=1:10, placing a mixture in a constant temperature water bath shaker, adjusting the temperature to 30° C., rotating at 160 rpm, and shaking and extracting for 1 h;

step S2: shaking and centrifuging an extract at 12,000 rpm at 4° C. for 25 min and passing it through a 0.45 micron filter membrane to obtain a leaching solution;

step S3: adding 10 mL of the leaching solution to a petri dish, using deionized water as a control sample, and respectively sowing 10 wild celery herb seeds evenly;

step S4: culturing in a constant temperature and humidity cabinet at 20° C. for 48 hours, using the wild celery herb seeds cultured in deionized water under the same conditions as a control sample to determine the germination rate of the seeds and the root length of germinated seeds, and calculating the ecotoxicity index $D_{st}$:

$$D_{st} = \frac{R_2 \times L_2}{R_1 \times L_1} \times 100$$

where, $D_{st}$ is the ecotoxicity of the test material, expressed in %; $R_1$ is the germination rate of control seeds, $L_1$ is the average root length of the control seeds, $R_2$ is the germination rate of the treated seeds, and $L_2$ is the average root length of the treated seeds.

The biodegradation rate index $D_{JJ}$ is obtained by the following steps:

step J1: preparing a test material and a reference material: preparing a decomposed compost with a fertilizer age of 2 to 4 months, using a thin-layer chromatography grade cellulose with a particle size of less than 20 microns as a positive control reference material, mixing it and the decomposed compost into a reference material at a standard dry weight ratio, and cutting a material to be tested into a size of 2 cm*2 cm and mixing with the same amount of the decomposed compost at the standard dry weight ratio as the test material; wherein the standard dry weight ratio of the decomposed compost in the test material and the material to be tested is 6:1;

step J2: loading and fermenting for composting: placing the mixed reference material, mixed text material, and the same amount of decomposed compost without adding any material respectively into a different reaction chamber body 7 for fermentation and composting, uniformly setting the temperature of the fermentation and composting treatment in each reaction chamber body 7 to 58° C., and uniformly adjusting the aeration rate of the air inlet 18 of each reaction chamber body 7 to 1.2 L/min;

step J3: measuring the biodegradation rate index DJJ: drying the air discharged from an air outlet 19 of each reaction chamber body 7 with a color-changing silica gel, then respectively detecting with a carbon dioxide detector the amount of carbon dioxide discharged from the mixed reference material, the mixed test material, and the same amount of decomposed compost without adding any material during the fermentation and composting, and then calculating the biodegradation rate index $D_{JJ}$ according to the following formula:

$$ThCO_2 = M_{TOT} \times C_{TOT} \times \frac{44}{12}$$

$$D_{jj} = \frac{(CO_2)_T - (CO_2)_B}{ThCO_2} \times 100$$

where, $ThCO_2$ is the theoretical amount of carbon dioxide discharged from the test material, with a unit of gram per container, namely g/container; $M_{TOT}$ is the total dry solids in the test material added to the compost container at the beginning of the test, with a unit of gram; $C_{TOT}$ is the ratio of total organic carbon to the total dry solids in the test material; and 44 and 12 respectively represent the molecular weight of carbon dioxide and the atomic weight of carbon; $(CO_2)_T$ is the cumulative amount of carbon dioxide discharged from each compost container (reaction chamber monomers 1 and 2 or 3 and 4) containing the test mixture, in grams per container, namely g/container; $(CO_2)_B$ is the mean cumulative amount of carbon dioxide evolved in the blank vessels(reaction chamber monomers 5 and 6), in grams per container;

step J4: drawing a biodegradation curve (a relationship curve of the biodegradation rate and time) of the test material and the reference material, and reading the average biodegradation rate value from a flat part of the biodegradation curve.

Therefore, the present application can separately control the reaction conditions inside each reaction chamber monomer installed on the device frame by using the electrical control cabinet, realize high-temperature fermentation of the small pile of materials in the chamber by using the electric heating plate and the thermal insulation material on the side wall of the reaction chamber monomer, and collect the leachate produced after the fermentation of the materials in the chamber with the leachate collection box so as to ensure that the comprehensive measurement process of biodegradability can be carried out in strict accordance with the standard fermentation indicators. The present application can also realize automatic discharging through the discharging mechanism at the bottom of the reaction chamber monomer and the material receiving trolley in conjunction with the rotation of the stirring paddle in the chamber, thereby reducing manual operation. The stirring paddle in the chamber can mix the materials in the chamber evenly during the reaction so as to avoid opening the chamber cover during the reaction and leaking odor and heat in the chamber, thereby ensuring that the reaction process is standard and controllable.

Figure 2:
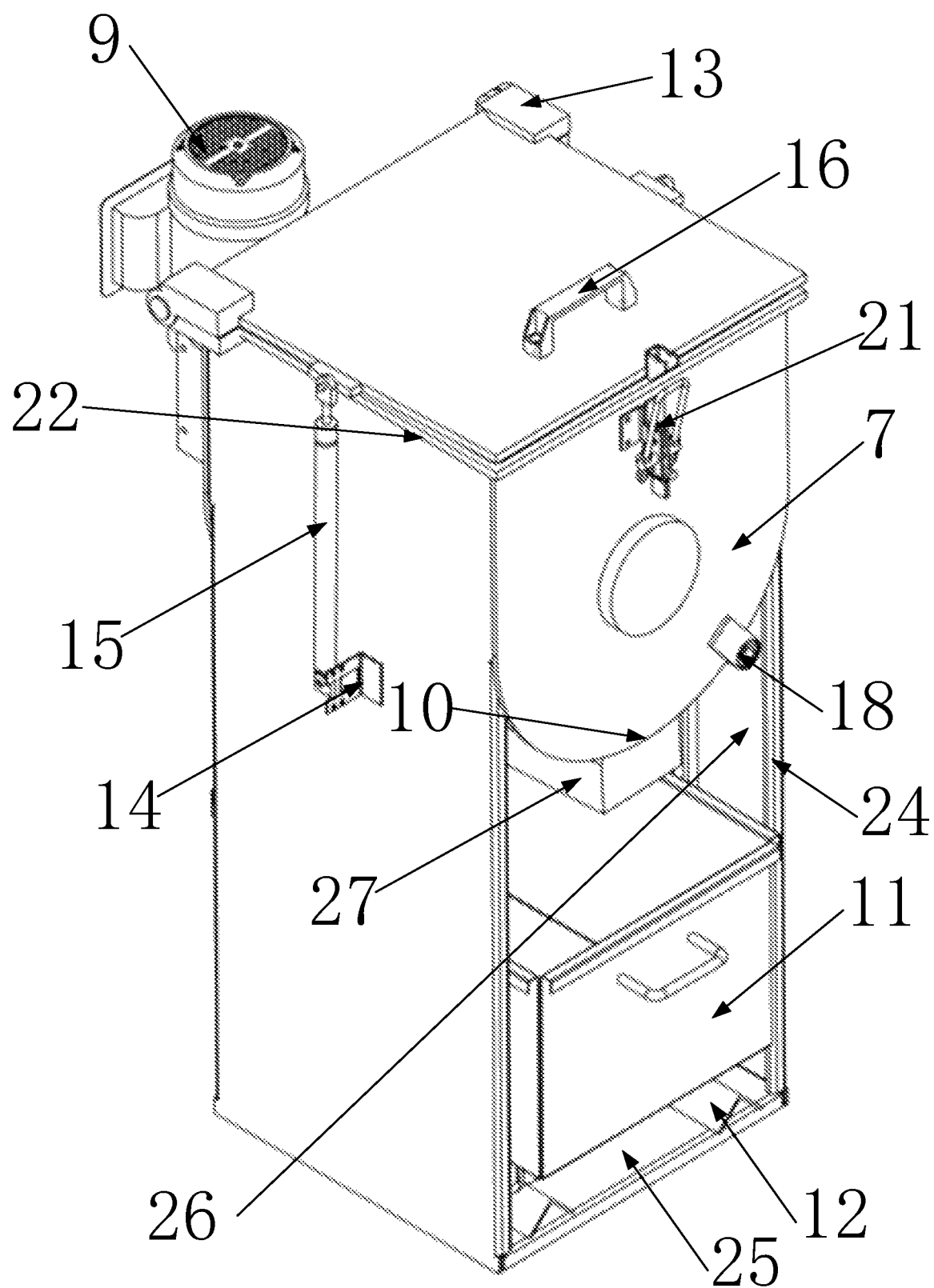
FIG. 2 is a schematic diagram of a reaction chamber monomer in FIG. 1.

When specifically implementing the above-mentioned reaction apparatus for comprehensively measuring biodegradability of a material, the bottom of the device frame 1 is further provided with a weight sensor at a position corresponding to each reaction chamber monomer 2 for measuring the weight of materials put into the chamber and displaying it on the control panel 5 of the electrical control cabinet;

A universal wheel 23 can be further provided under the device frame 1 to facilitate the movement of the apparatus;

The front part of the device frame 1 can further be used to separately seal each reaction chamber monomer 2 through a door panel 4;

Refer to FIG. 2. The outside of the reaction chamber monomer 2 can further be arranged to be supported by respectively independent support frames 24, and each support frame comprises:

a side vertical plate 26, which is arranged on both sides of the support frame 24, and is connected and fixed to the side wall of the reaction chamber body 7;

a support base plate 25, which is connected to the bottom of the support frame 24, wherein the support base plate 25 is further provided with a sliding rail 12 extending from back to front, the material receiving trolley 11 moves back and forth along the sliding rail 12 for taking out the fermentation material that falls into it or for receiving the fermentation material that falls from the reaction chamber body 7;

and after the reaction chamber monomer 2 is installed on the device frame 1, the support base plate 25 of the reaction chamber monomer 2 is located above the weight sensor to trigger the weight sensor to collect the weight of materials in the reaction chamber monomer 2 and the chamber thereof.

In the reaction chamber monomer 2, the chamber cover 6 of the reaction chamber body 7 can be made of a reduced resin material to provide heat preservation and heat insulation. The lower edge of the chamber cover can further be provided with a sealing strip 22 to seal the reaction chamber body 7, so as to ensure that the entire reaction chamber body 7 only discharges air from the chamber through an air outlet 19 to realize the measurement of carbon dioxide produced during the fermentation reaction of the materials in the chamber;

A buckle 21 is further provided between the chamber cover 6 and the reaction chamber body, when the buckle 21 is locked, the chamber cover 6 and the top of the reaction chamber body 7 are sealed and connected through the sealing strip 22;

A handle 16 is further provided on the top of the chamber cover 6, the side of the chamber cover 6 is further connected with the air spring 15, the lower end of the air spring 15 is connected with a cylinder hinge seat 14 arranged on the outside of the side vertical plate 26, the chamber cover 6 can respond to an opening signal triggered by the electrical control cabinet to be driven by the air spring 15 to rotate upwards to open the reaction chamber body 7 for placing reaction materials with the fixed supporting rotating plate 13 provided at the top of the rear side of the reaction chamber body 7 as the rotating shaft or to rotate downwards to seal the reaction chamber body 7 to provide a closed and controllable reaction environment.

Figure 3:
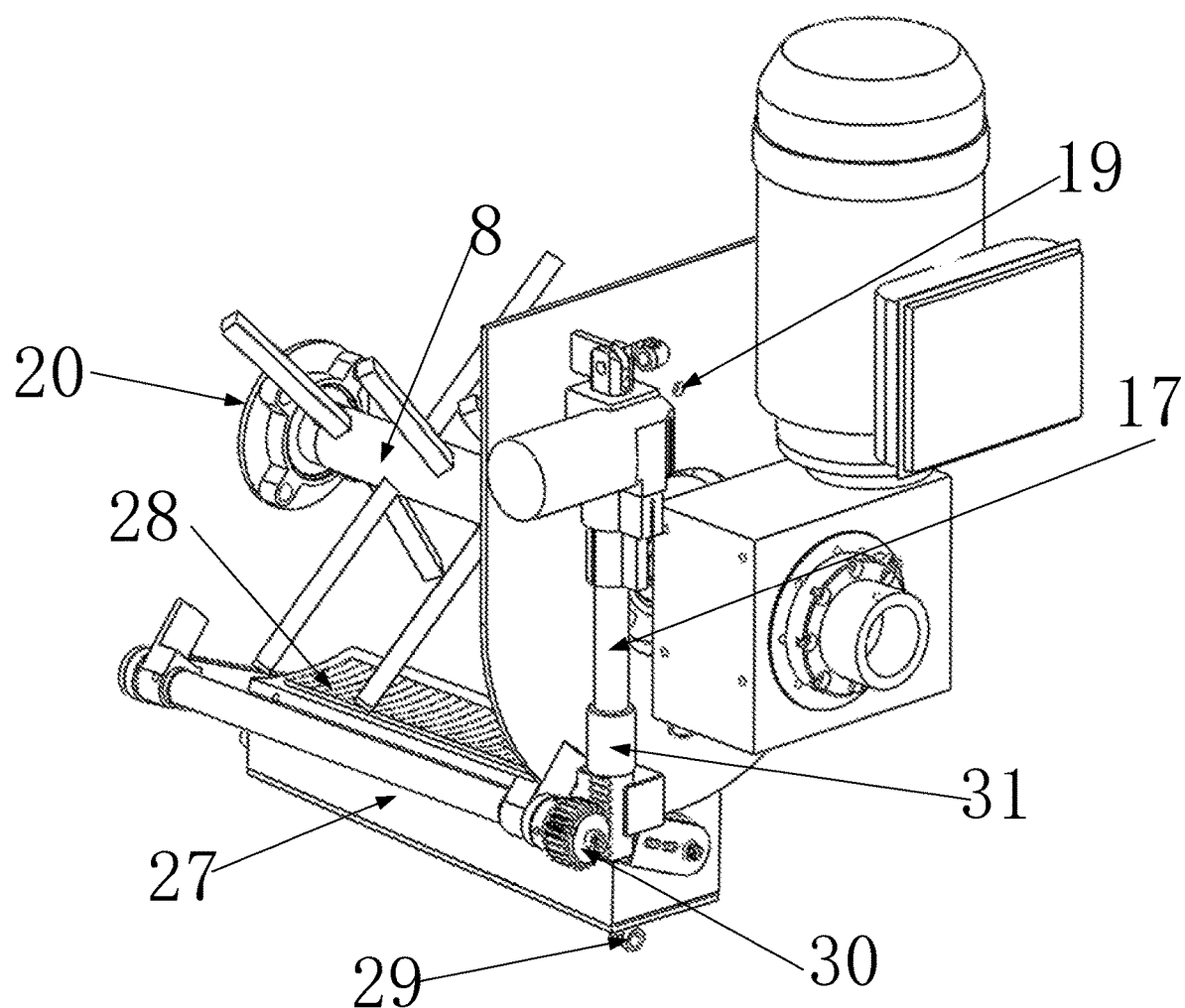
FIG. 3 is a schematic diagram of a structure of a discharging mechanism according to the present application.
Figure 5:
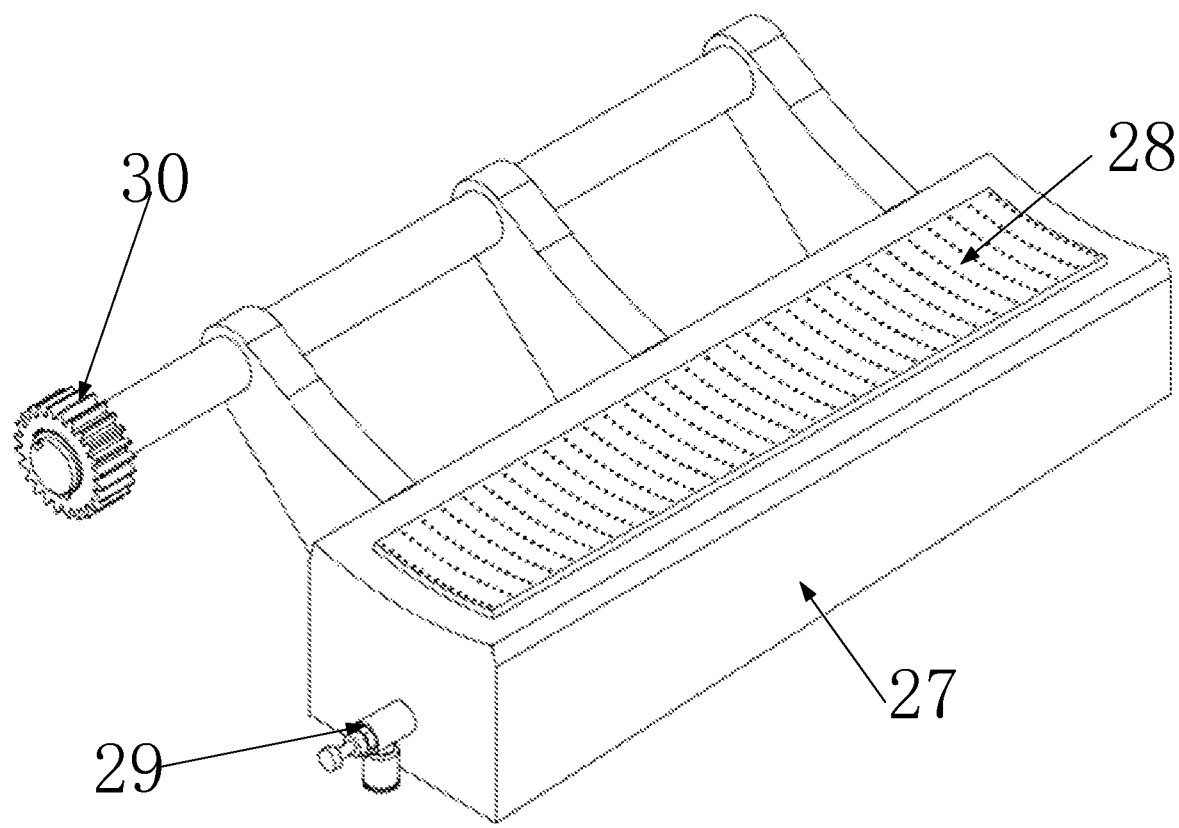
FIG. 5 is a schematic diagram of a structure of a leachate collection box used in the present invention.

Refer to FIG. 3. As for the discharging mechanism 10 provided in the present application, the bottom of the leachate collection box 27 is arranged to be low in the front and high in the back, and the top of the leachate collection box 27 is matched with the arc structure of the discharge port of the reaction chamber body 7 correspondingly so that it can closely fit the receiving port of the leachate receiving port, the leachate receiving port is closed by an arc-shaped stainless steel filter screen 28 to isolate the solid fermentation products in the chamber so that only the leachate can pass through the arc-shaped stainless steel filter screen 28 to be collected into the leachate receiving port. In accordance with the inclination angle of the bottom of the leachate collection box 27, in the present application, a leachate adjustment ball valve 29 can be connected to the lower part of the front end of the leachate collection box 27 that accumulates relatively much leachate, and the leachate adjustment ball valve 29 is connected to a drain pipe to control the discharge of the leachate received in the leachate collection box 27 so as to prevent the leachate from affecting the reaction of the materials in the chamber;

The pore size of the curved stainless steel filter screen 28 can be set to 1 mm so as to fully prevent fine fermentation materials from falling into the leachate collection box and affecting the accuracy of subsequent measurement, and at the same time to ensure the filtration of the leachate after fermentation;

One side of the leachate collection box 27 can be connected with a rotating shaft parallel to the edge of the leachate collection box 27 as shown in FIG. 5 through an intermediate connecting piece. The rear end of the rotating shaft is fixedly provided with a gear 30. The gear 30 meshes with a rack 31 vertically arranged on the rear side of the reaction chamber body 7, and the upper end of the rack 31 is fixedly connected to an electric push rod 17 fixedly arranged on the rear side of the reaction chamber body 7. Thereby, the electric push rod 17 can be extended downward or retracted upward correspondingly in response to the control signal of the electrical control cabinet 3. When the electric push rod 17 is extended downward, its end rack engages and drives the gear 30 to rotate in a first direction to drive the rotating shaft to rotate in the opening direction, so that the leachate collection box 27 rotates downwards and leaves the discharge port at the bottom of the reaction chamber body 7 so as to make the fermentation material inside the reaction chamber body 7 fall into the material receiving trolley 11. When the electric push rod 17 is retracted upwards, its end rack engages and drives the gear 30 to rotate in a second direction to drive the rotating shaft to rotate in the closing direction, so that the leachate collection box 27 rotates upwards and the upper side of the leachate receiving port of the leachate collection box 27 is tightly attached to the periphery of the discharge port located at the bottom of the reaction chamber body 7, and the electric push rod 17 is used to drive the gear rack to provide an upward turning torque, so that the leachate collection box 27 is tightly attached upwards or is even in an interference fit condition. The discharge port is closed to ensure that the interior of the reaction chamber body 7 is completely sealed during the reaction. The reaction air is provided only through the air inlet at an aeration rate required by the standard, and the reacted carbon dioxide gas is discharged through an air outlet accordingly so that the carbon dioxide detector can determine the amount of carbon dioxide emitted during fermentation and composting of the test material.

Figure 4:
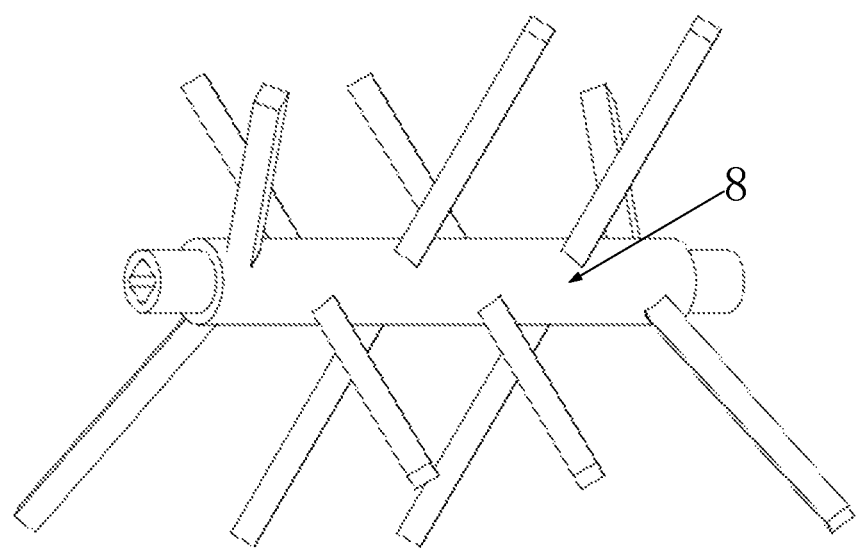
FIG. 4 is a schematic diagram of a structure of a stirring paddle in a reaction chamber monomer used in the present invention.

The stirring paddle 8 inside the reaction chamber body 7 can be specifically provided as shown in FIG. 4, with a drive shaft horizontally arranged between a motor output shaft and an plug-in flange 20 installed on the front side of the inner wall of the reaction chamber body 7, and blades evenly arranged on the periphery of the drive shaft at an angle of 90°. It is controlled by the electrical control cabinet and rotates according to the set turning frequency during the fermentation of the materials in the chamber to stir and mix the materials in the chamber, and it can also rotate when the leachate collection box 27 is separated from the discharge port located at the bottom of the reaction chamber body 7 to drive to turn over the fermentation material in the chamber and discharge it into the material receiving trolley 11 through the discharge port. The plug-in flange 20 can be connected to the front end of the stirring paddle 8 through a bolt structure to provide support for the stirring paddle 8 so as to prevent it from being deformed and broken when it turns over the material in the chamber. The plug-in flange 20 and the stirring blade 8 are detachably connected to facilitate replacement of a stirring blade when it is deformed due to failure. As a result, the service life of the measurement apparatus of the present application can be effectively extended.

Therefore, the present application accurately controls the material fermentation according to the fermentation conditions of different measurement standards through six reaction chamber monomers to perform measurement of different degradability, or accurately sets the reaction chamber monomers to the same fermentation conditions so as to compare with the reference material. In the present application, a flow regulating valve is installed in the electrical control cabinet, and it is connected to the air inlet through a hose to precisely control the air intake of the reaction chamber. In the present application, the stirring paddle in the reaction chamber monomer can be directly used for automatically turning the materials without opening the chamber cover or leaking the fermentation stink. In the present application, an electric heating plate and a thermal insulation cotton are further attached to both sides of the chamber to form a thermal insulation and heating chamber. The leachate collection box located at the bottom of the chamber can effectively discharge the fermentation leachate, realize the sealing of the chamber during the reaction, and open the discharge port to discharge the fermentation material from the chamber after the reaction is completed. In the present application, sealing is realized by providing two air springs and four buckles between the chamber cover and chamber of the reaction chamber monomer. A discharge cover adopts an electric push rod to ensure the air tightness of the apparatus. The present apparatus is equipped with a weight sensor, a temperature sensor, a motor, an air compressor and an electric heating plate and a discharging mechanism drive motor, all of which are electrically connected to the PLC controller so as to realize automatic operation and automatic data recording. The present invention can comprehensively determine the disintegration rate index BJ, the ecotoxicity index ST and the biodegradation rate index JJ of the test material, so that the comprehensive evaluation of the bioavailability of materials can be realized according to the degradation rate, disintegration rate and ecological non-toxicity of materials subsequently in a weighted comprehensive evaluation method. The advantages of the present invention are that the measurement apparatus can accurately control air supply, temperature, turning and water discharge, and has good air tightness, and the measurement method can comprehensively detect the degradability of materials from various aspects. The data obtained by the present invention has high accuracy and the results are highly reliable, and can be used as an effective apparatus and method for evaluating the degradability of materials.

The above are only the implementation manners of the present application, and the description is relatively specific and detailed, but it should not be understood as a limitation to the scope of the present application. It should be pointed out that an ordinary person skilled in the art can make a plurality of modifications and improvements without departing from the concept of the present application, and these all fall within the protection scope of the present application.

The invention claimed is:
1. A reaction apparatus for comprehensively measuring biodegradability of a material, wherein it comprises:
   a device frame;
   an electrical control cabinet, which is arranged on the device frame, wherein a control panel is installed on a surface of the electrical control cabinet, and a programmable logic controller is provided inside the control panel;
   a plurality of reaction chamber monomers arranged on the device frame, wherein each of the reaction chamber monomers is respectively connected to the electrical control cabinet, and the reaction chamber monomers are independent of each other and are respectively controlled by the electrical control cabinet, wherein the reaction chamber monomer comprises:
   a reaction chamber body, which is arranged on an upper side of an inside of the reaction chamber monomer, wherein the top of the reaction chamber body is sealed by a chamber cover, materials required for measurement can be put into the reaction chamber body after the chamber cover is opened, an electric heating plate and a thermal insulation cotton are attached to a side wall of the reaction chamber body, the electric heating plate is controlled by the electrical control cabinet to adjust the temperature in the reaction chamber body; and the bottom of the reaction chamber body is provided with a discharge port for discharging the materials from the chamber;
   a stirring paddle, which is arranged inside the reaction chamber body, wherein a rear end of the stirring paddle is connected to a motor installed on a rear side of the reaction chamber body, and the electrical control cabinet controls the operation of the motor to drive the stirring paddle to turn over the materials in the reaction chamber body;
   an air inlet, which is arranged on a front side wall of the reaction chamber main body, wherein the air inlet is connected to the inside of the reaction chamber body for adjusting an air intake time inside the reaction chamber body according to a control signal output by the electrical control cabinet;
   an air outlet, which is arranged on the rear side of the reaction chamber body, wherein one end of the air outlet is connected to the inside of the reaction chamber body, and the other end of the air outlet is dried by a color-changing silica gel and is then connected to a carbon dioxide detector;
   a discharging mechanism, comprising a leachate collection box arranged below the reaction chamber body, wherein when the leachate collection box abuts against the discharge port at the bottom of the reaction chamber body, the leachate collection box is used for receiving the leachate produced during fermentation process in the chamber; and when the leachate collection box is separated from the discharge port at the bottom of the reaction chamber body, and the leachate collection box is used for discharging the fermentation material in the chamber;
   a material receiving trolley, which is arranged on a lower side of the inside of the reaction chamber monomer and located below the leachate collection box, wherein the top of the material receiving trolley is of an open structure for receiving the fermentation material discharged through the discharge port at a bottom of the reaction chamber body:
   wherein the bottom of the device frame is further provided with a weight sensor at a position corresponding to each reaction chamber monomer:
   an outside of the reaction chamber monomer is further provided with a support frame, comprising:
   a side vertical plate, which is arranged on both sides of the support frame and is connected and fixed to the side wall of the reaction chamber body:
   a support base plate, which is connected to a bottom of the support frame, wherein the support base plate is further provided with a sliding rail extending from back to front, the material receiving trolley moves back and forth along the sliding rail for receiving the fermentation material that falls from the reaction chamber body:
   and after the reaction chamber monomer is installed on the device frame, the support base plate of the reaction chamber monomer is located above the weight sensor to trigger the weight sensor to collect the weight of materials in the reaction chamber monomer.

2. The reaction apparatus for comprehensively measuring biodegradability of a material according to claim 1,
   wherein the chamber cover is made of a reduced resin material, and a sealing strip is provided on a lower edge of the chamber cover;
   a buckle is further provided between the chamber cover and the reaction chamber body, when the buckle is locked, the chamber cover and the top of the reaction chamber body are sealed and connected through the sealing strip.

3. The reaction apparatus for comprehensively measuring biodegradability of a material according to claim 1, wherein a handle is further provided on the top of the chamber cover, the side of the chamber cover is further connected with an air spring, a lower end of the air spring is connected with a cylinder hinge seat arranged on an outside of the side vertical plate, the chamber cover is driven by the air spring rotate upward to open or to rotate downward to close the reaction chamber body with a fixed supporting rotating plate arranged at the top end of the rear side of the reaction chamber body as a rotating shaft.

4. The reaction apparatus for comprehensively measuring biodegradability of a material according to claim 1, wherein the bottom of the leachate collection box is arranged to be low in the front and high in the back, the lower part of the front end of the leachate collection box is further connected with a leachate regulating ball valve, and the leachate regulating ball valve discharges the leachate received in the leachate collection box; and when the leachate collection box is separated from the discharge port located at the bottom of the reaction chamber body, the stirring paddle inside the reaction chamber body rotates to drive to turn over the fermentation material in the chamber and discharge it from the discharge port into the material receiving trolley.

5. The reaction apparatus for comprehensively measuring biodegradability of a material according to claim 1, wherein one side of the leachate collection box is connected with a rotating shaft, the rear end of the rotating shaft is fixedly arranged with a gear, the gear meshes with a rack vertically arranged on the rear side of the reaction chamber body, and the upper end of the rack is fixedly connected to an electric push rod fixedly arranged on the rear side of the reaction chamber body;

the electric push rod is controlled by the electrical control cabinet to extend downward or retract upward, during the downward extension of the electric push rod, the gear is driven to rotate in a first direction to drive the rotating shaft to rotate in the opening direction so that the leachate collection box rotates downwards and leaves the discharge port at the bottom of the reaction chamber body so as to make the fermentation material inside the reaction chamber body fall into the material receiving trolley; when the electric push rod is retracted upwards, the gear is driven to rotate in a second direction to drive the rotating shaft to rotate in the closing direction, so that the leachate collection box rotates upwards and closely fits the discharge port at the bottom of the reaction chamber body to close the discharge port.

* * * * *